US00PP15620P2

(12) United States Plant Patent
Olesen et al.

(10) Patent No.: US PP15,620 P2
(45) Date of Patent: Mar. 1, 2005

(54) ROSE PLANT NAMED 'POULEN010'

(50) Latin Name: *Rosa hybrida*
Varietal Denomination: POULen010

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/742,413

(22) Filed: Dec. 22, 2003

(51) Int. Cl.[7] ..... A01H 5/00
(52) U.S. Cl. ..... Plt./138

(58) Field of Search ..... Plt./138, 137, 148, Plt./149, 107

(56) References Cited

U.S. PATENT DOCUMENTS

PP12,999 P2 * 9/2002 Olesen et al. ..... Plt./102

* cited by examiner

*Primary Examiner*—Anne Marie Grunberg
*Assistant Examiner*—June Hwu

(57) ABSTRACT

A new garden rose plant of the hybrid tea class which has abundant, deep pink flowers and attractive foliage. This new and distinct variety has shown to be uniform and stable in the resulting generations from asexual propagation.

2 Drawing Sheets

Botanical classification: *Rosa hybrida.*
Variety denomination: 'POULen010'.

SUMMARY OF THE INVENTION

The present invention constitutes a new and distinct variety of garden rose plant which originated from a controlled crossing between an unnamed female parent plant, and a male parent 'Harmusky', non-patented. The two parents were crossed during the summer of 1996 and the resulting seeds were planted in a controlled environment in Fredensborg, Denmark. The new variety is named 'POULen010'.

The new variety may be distinguished from its seed parent, by the following combination of characteristics:

1. Whereas seed parent has a light pink flower color, 'POULen010' has a light red to a deep pink flower color.
2. The seed parent has a 10 to 20 petals. 'POULen010' has 50 petals.
3. The seed parent has little to no scent, while 'POULen010' has a strong, floral scent.

The new variety may be distinguished from its pollen parent, 'Harmusky' by the following combination of characteristics:

Whereas the pollen parent has a medium pink flower color, 'POULen010' has a light red to deep pink flower color.

The objective of the hybridization of this rose variety was to create a new and distinct variety for garden use with unique qualities, such as:

1. Uniform and abundant deep pink flowers;
2. Vigorous, but compact growth when propagated both as a budded rose and on its own roots;
3. Disease resistance;
4. Exceptional fragrance.

This combination of qualities is not present in previously available commercial cultivars of this type, known to the inventors, and distinguish 'POULen010' from all other varieties of which we are aware.

As part of their rose development program, L. Pernille Olesen and Mogens N. Olesen germinated the seeds from the aforementioned hybridization during winter 1996 and conducted evaluations on the resulting seedlings in a controlled environment in Fredensborg, Denmark.

'POULen010' was selected in the spring 1997 by the inventors as a single plant from the progeny of the aforementioned hybridization.

Asexual reproduction of 'POULen010' by traditional budding and rooted cuttings was first done by L. Pernille and Mogens N. Olesen in their nursery in Fredensborg, Denmark in June, 1997. This initial and other subsequent asexual propagations conducted in controlled environments have demonstrated that the characteristics of 'POULen010' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULen010'.

Specifically illustrated in: SHEET 1:

FIG. 1.1; Open flower, stem showing cluster of open flowers, branching, and the attachment of leaves, buds, and peduncles;

FIG. 1.2; Flower bud closed, flower bud as sepals unfold, and partially open;

Specifically illustrated in SHEET 2:

FIG. 2.1; Flower petals, detached;

FIG. 2.2; Sepals, receptacle, and peduncle;

FIG. 2.3; Bare stems exhibiting thorns;

FIG. 2.4; Mature leaf.

DETAILED DESCRIPTION OF THE VARIETY

The following is a description of 'POULen010', as observed in its growth in a field nursery in Jackson County, Oreg. Observed plants are 3 years of age, grown on *Rosa multiflora* understock. Color references are made using The Royal Horticultural Society (London, England) Colour Chart, 1995, except where common terms of color are used.

For a comparison, several physical characteristics of the rose variety 'POULdra', a rose variety from the same inventors described and illustrated in U.S. Plant Pat. No. 12,999 dated Sep. 24, 2002 are compared to 'POULen010' in Chart 1.

CHART 1

| | 'POULen010' | 'POULdra' |
|---|---|---|
| General Tonality | Red-Purple Group 67C. | Red-Purple Group 57B. |
| Petalage | 50. | 20 to 30. |
| Flower diameter | 60 mm. | 100 mm. |

Parents:

*Seed parent.*—Unnamed seedling.

*Pollen parent.*—'Harmusky'.

FLOWER AND FLOWER BUD

Blooming habit: Recurrent.

Flower bud:

*Size.*—Upon opening, 25 mm in length from base of receptacle to end of bud.

*Bud form.*—Broad based pointed ovoid.

*Bud color.*—As sepals unfold, petals are Red-Purple Group 66A. At ¼ opening petals are Red-Purple Group 66A. Sepals: Size: 20 mm (l)×9 mm (w). Upper Surface: Color: Yellow-Green Group 138A to Yellow-Green Group 145B. Surface: Strongly pubescent. Lower Surface: Color: Yellow-Green Group 144B with anthocyanic pigments the color of Greyed-Purple Group 185A. Surface: Mildly pubescent. Shape: Sepal apex is cirrose. Base is flat at union with receptacle. Margins: Weak foliaceous appendages on three of the five sepals. Stipitate Glands: Present in medium quantity on margins of the sepals.

*Receptacle.*—Surface Texture: Smooth. Shape: Urn-shaped. Size: 6 mm (h)×7 mm (w). Color: Yellow-Green Group 144A. Anthocyanin: Greyed-Red Group 181A.

*Peduncle.*—Surface: Fragrant stipitate glands in abundant to medium quantity. Length: 30 to 35 mm. Diameter: 2 to 3 mm. Color: Yellow-Green Group 144A. Anthocyanin: Very light Greyed-Purple Group 184C. Strength: Strong.

*Borne.*—Multiples of 5 to 9 buds per flowering stem.

Flower bloom:

*Fragrance.*—Strong floral perfume-like scent.

*Duration.*—The blooms have a duration on the plant of approximately 10 to 14 days. Afterwards, petals fall cleanly away from plant.

*Size.*—Average flower diameter is 60 mm when open.

*Form.*—Flowers form a deep cup with outer petals slightly overlapping. Shape of flower when viewed from the side: Upon opening, upper part: Flat. Upon opening, lower part: Flat. Open flower, upper part: Flattened convex. Open flower, lower part: Concave.

*Petalage.*—50 petals under normal conditions with 10 petaloids.

*Color.*—

*Upon opening, petals.*—Outermost petals: Outer side is Red-Purple Group 57C. Distinct intonations of White Group 155B form a vertical line which bisects the petal. Inner side petal coloration is Red-Purple Group 66A. Innermost petals: Outer side is Red-Purple Group 57C. Distinct intonations of White Group 155B form a vertical line which bisects the petal. The inner side is Red-Purple Group 67C.

*Upon opening, basal petal spots.*—Outermost petals: Outer side: White Group 155B. Inner Side: White Group 155B. Innermost petals: Outer side: White Group 155B. Inner Side: White Group 155B.

*After opening, petals.*—Outermost petals: Outer side is Red-Purple Group 57C. Distinct intonations of White Group 155B form a vertical line which bisects the petal. The inner side is Red-Purple Group 67C. Innermost petals: Outer side is Red-Purple Group 57C. Distinct intonations of White Group 155B form a vertical line which bisects the petal. The inner side is Red-Purple Group 67C.

*After opening, basal petal spots.*—Outermost petals: Outer Side: White Group 155B. Inner Side: White Group 155B. Innermost petals: Outer Side: White Group 155B. Inner Side: White Group 155B.

General tonality: On open flower Red-Purple Group 67C. No change in the general tonality at the end of the 10th day. Afterwards, general tonality is Red-Purple Group 67C.

*Petals.*—Petal Reflex: Petals reflex slightly. Reflex is more pronounced in the outer petals. Margin: Entire and uniform. Medium undulations of margin. Shape: Apex: Round. Base: Acute. Size: 35 mm (l)×30 mm (w). Thickness: Thick. Arrangement: Not Formal.

*Petaloids.*—Quantity: 10 on average. Color: Red-Purple Group 66C. Size: 7 mm (l)×15 mm (w).

*Reproductive organs.*—Pistils: Length: 3 mm long. Quantity: 52 (actual count). Pollen: None observed. Anthers: Size: 2 mm in length. Color: Greyed-Orange Group 163C. Quantity: 90 (actual count). Filaments: Color: Red-Purple Group 61C. Length: 4 mm. Stigmas: Inferior in location to anthers. Color: Greyed-Yellow Group 161A. Styles: Color: Yellow-Green Group 150D. Other Intonations: Streaks of Red-Purple Group 61C observed at top of styles and extending into the stigmas. Hips: None Observed in the field nursery in Jackson County Oreg.

PLANT

Plant growth: Moderate, upright to bushy. Height is 100 to 150 cm. Spread is 100 cm.

*Stems.*—Color: Young wood: Yellow-Green Group 144B. Older wood: Yellow-Green Group 146C. Surface Texture: Young wood: Smooth. Older wood: Smooth. Thorns: Juvenile: Greyed-Orange Group 176A. Mature: Greyed-Yellow Group 162A.

*Plant foliage.*—Normal number of leaflets on normal leaves in middle of the stem: 5 leaflets.

*Compound leaf size.*—140 mm (l)×112 mm (w).

*Quantity.*—3 leaves per 10 cm of stem.

*Color.*—Mature Foliage: Upper Leaf Surface: Green Group 143A to 143B. Lower Leaf Surface: Yellow- Green Group 147C. Juvenile foliage: Upper Leaf Surface: Yellow-Green Group 144B. Lower Leaf Surface: Yellow-Green Group 145A. Anthocyanin: Location: Margins of juvenile leaflets. Color: Greyed-Red Group 181C.

Plant leaves and leaflets:

*Stipules.*—Size: 20 mm in length. Color: Yellow-Green Group 144B. Margins: Finely serrated. Few to abundant stipitate glands.

*Petiole.*—Length: 20 mm. Color: Yellow-Green Group 145A. Underneath: Thorns observed. Anthocyanin: Greyed-Red Group 181C to 181D observed.

*Rachis.*—Length: 50 mm. Color: Yellow-Green Group 145A. Underneath: Thorns observed.

*Leaflet.*—Size: Terminal leaflets on normal leaves. 40 to 60 mm (l)×22 to 42 mm (w). Edge: Serrated. Shape: Generally ovate. Apex: Acute to slightly cuspidate. Base: Rounded and slightly acute. Texture: Smooth. Arrangement: Odd pinnate. Venation: Reticulate. Glossiness: Matte finish. Thickness: Thick.

Disease resistance: Above average resistance to mildew, rust, black spot, and Botrytis under normal growing conditions in Jackson County, Oreg.

Cold hardiness: The variety 'POULen010' has been found to be cold tolerant to USDA Cold Hardiness Zone 6.

What is claimed is:

1. A new and distinct variety of rose plant of the hybrid tea rose class, substantially as herein illustrated and described as a distinct and novel rose variety due to its abundant deep pink, disease resistance, and extended period of bloom.

* * * * *

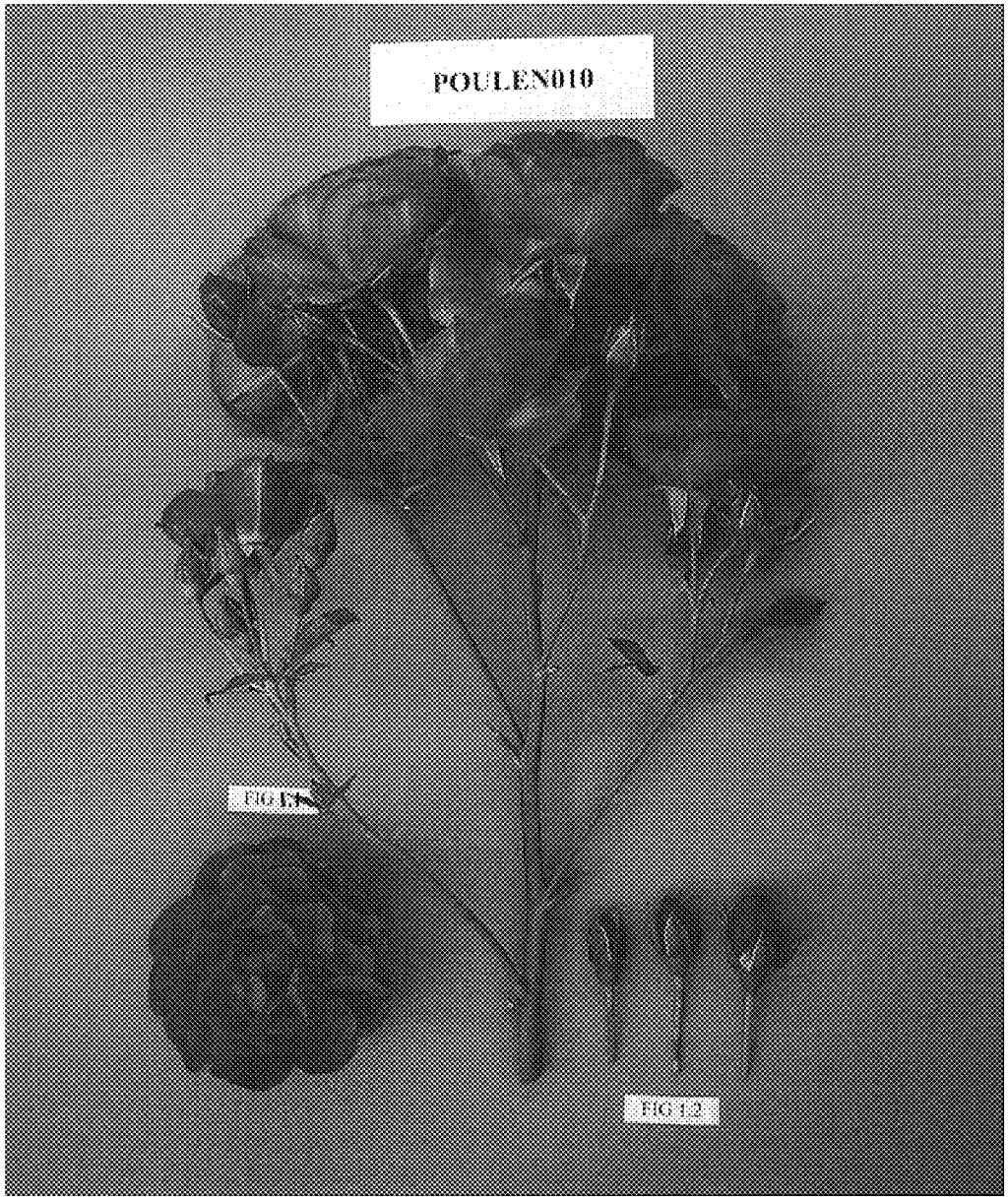
POULEN010
FIG 1.1
FIG 1.2

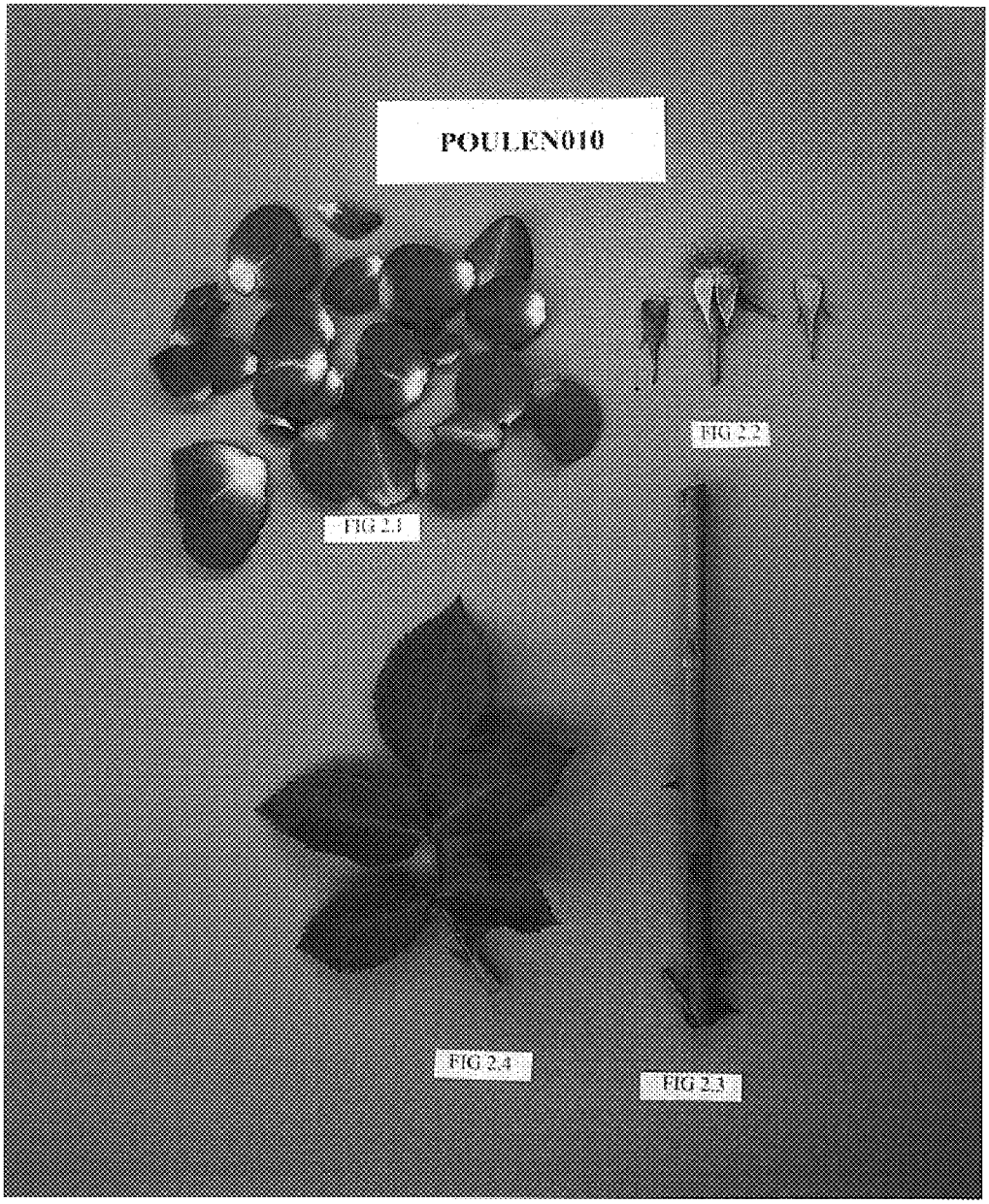
POULEN010
FIG 2.1
FIG 2.2
FIG 2.3
FIG 2.4